United States Patent [19]

De Rosa

[11] 4,033,354

[45] July 5, 1977

[54] COOLING GARMENT

[76] Inventor: Maria I. De Rosa, 1928 Strawbridge Drive, Library, Pa. 15129

[22] Filed: Dec. 5, 1975

[21] Appl. No.: 595,238

[52] U.S. Cl. .................. 128/379; 128/402
[51] Int. Cl.² ........................... A61N 5/00
[58] Field of Search ......... 128/402, 403, DIG. 15, 128/379, 384, 385, 399, 359; 2/DIG. 6, DIG. 7, 7

[56] References Cited

UNITED STATES PATENTS

| | | | |
|---|---|---|---|
| 2,357,851 | 9/1944 | Scheyer | 2/7 UX |
| 2,697,424 | 12/1954 | Hanna | 128/403 |
| 2,766,757 | 10/1956 | Zelony | 128/359 |
| 3,644,705 | 2/1972 | Johnson | 128/379 |
| 3,885,403 | 5/1975 | Spencer | 128/403 |
| 3,939,842 | 2/1976 | Harris | 128/401 |
| 3,950,789 | 4/1976 | Konz et al. | 2/DIG. 6 |

Primary Examiner—Lawrence W. Trapp
Attorney, Agent, or Firm—Parmelee, Miller, Welsh & Kratz

[57] ABSTRACT

An ice cooling garment to alleviate physiological strain due to heat stress. Sealed pockets containing water are removably attached within a vest-like garment securable around the body of an individual. The water-filled pockets are frozen and subsequently attached to the inside of the garment so as to provide body cooling under heat stress conditions such as in mine rescue work.

10 Claims, 5 Drawing Figures

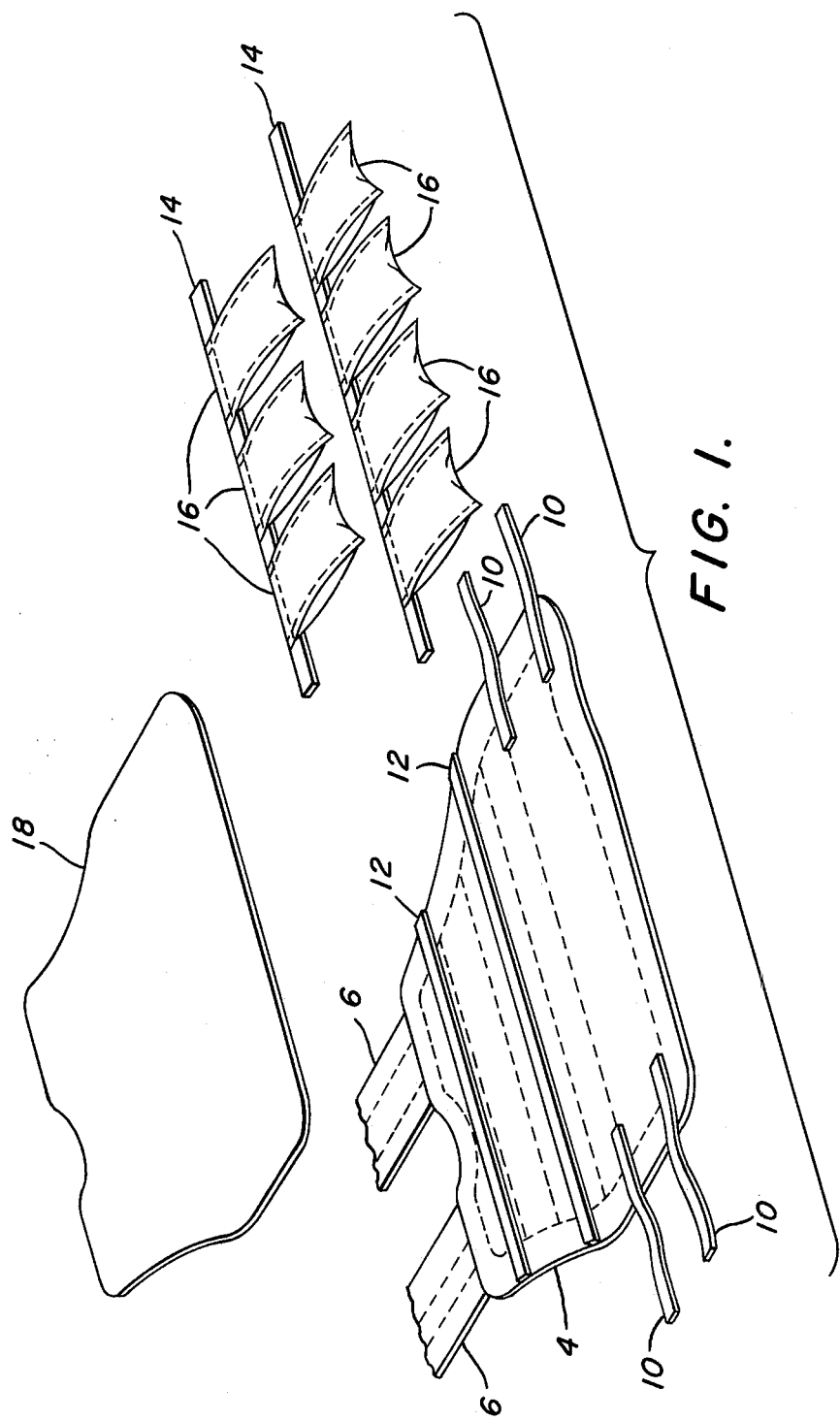

COOLING GARMENT

GOVERNMENT RIGHTS

The Government has a non-exclusive, irrevocable, royalty-free license for governmental purposes in this invention.

BACKGROUND OF THE INVENTION

1. Field of the Invention

The present invention relates generally to devices for personal cooling under heat stress conditions, and more specifically to personal cooling garments containing ice for use in hot environments, such as in mine rescue work.

2. Prior Art

Several types of cooling garments have been developed to alleviate heat stress problems encountered by workers in hot environments. One type of garment uses cold water that is mechanically pumped and channeled through thin tubes running throughout the garment. A second type of garment uses dry ice inserted into pockets in the garment and a third type developed in South Africa for gold mine workers uses ice. Details regarding cooling garments of each of these types may be found in the references section of Bureau of Mines Report of Investigations No. 8139 "An Ice Cooling Garment for Mine Rescue Teams" by Maria DeRosa and Richard Stein, 1976. In cold water cooling garments, the water is channeled through inner tubing and a small rupture is sufficient to render the entire garment in-effective. Such garments require a mechanical pump and a bucket of ice which are subject to failure and make the garment bulky and uncomfortable to carry. These additional parts also contribute to a high cost for such garments. Dry ice cooling garments utilize solid $CO^2$ which sublimates rapidly and needs to be replaced every few hours. This results in extra expense, inconvenience and consumption of time. Also, because of the extreme low temperature of dry ice, insulation is required between the dry ice pockets and the wearer so as to prevent dangerous contact between the dry ice and the wearer. This insulation reduces the cooling effectiveness of the garment. Repairs of such garments in case of a bad rupture are generally costly. Current ice cooling garments utilize an excessive amount of ice, the physical dimensions of which make the garment bulky. The duration of the ice in its frozen state in such garments is generally only about two hours and since the ice bags are sewed to the jacket, the whole garment needs to be frozen which requires large freezers, large amounts of energy and longer freezing times. Having the pockets sewed to the jacket also results in the ice being exposed only on one side which reduces air circulation to the ice and reduces the cooling ability of the jacket. Having the bags sewed to the jacket also makes repairs more difficult and costly. Insulation in such garments is provided by a second garment which requires the wearing of two garments. This makes the overall garment uncomfortable to wear for long periods of time.

SUMMARY OF THE INVENTION

The present invention is a vest-like garment for cooling the body of the wearer. An insulated front body panel and an insulated rear body panel are attached together by shoulder straps which connect the top of the front body panel to the top of the rear body panel. First fasteners, such as those known by the trademark Velcro, are secured to the sides of the front body panel, and second fasteners, which are releasably attachable to the first fasteners, are secured to the sides of the rear body panel such that when the first fasteners are secured to the second fasteners the garment is secured to the body of the wearer. Third fasteners are attached to the inside of the front and rear body panels, and a plurality of sealed water-proof bags filled with water are secured to a plurality of fourth fasteners which are releasably attachable to the third fasteners, such that when the sealed water-proof bags are frozen and releasably secured to the inside of the garment by securing the fourth fasteners to the third fasteners, the garment cools the body of the wearer. The sealed water-proof bags are preferably formed from a vinyl plastic and are preferably arranged on the body panels in two rows of pockets. A layer of absorbent fabric such as terry cloth may be disposed between the inside surface of the bags and the wearer of the garment. The front and back body panels are preferably made from two layers of fabric such as an aluminized rubberized dacron, with an insulating foam layer between the two layers of fabric.

DESCRIPTION OF THE DRAWINGS

FIG. 1 is an exploded perspective view of one of the body panels of the present invention showing the positioning of the sealed water-proof bags thereon.

DESCRIPTION OF THE PREFERRED EMBODIMENT

Figure 2:
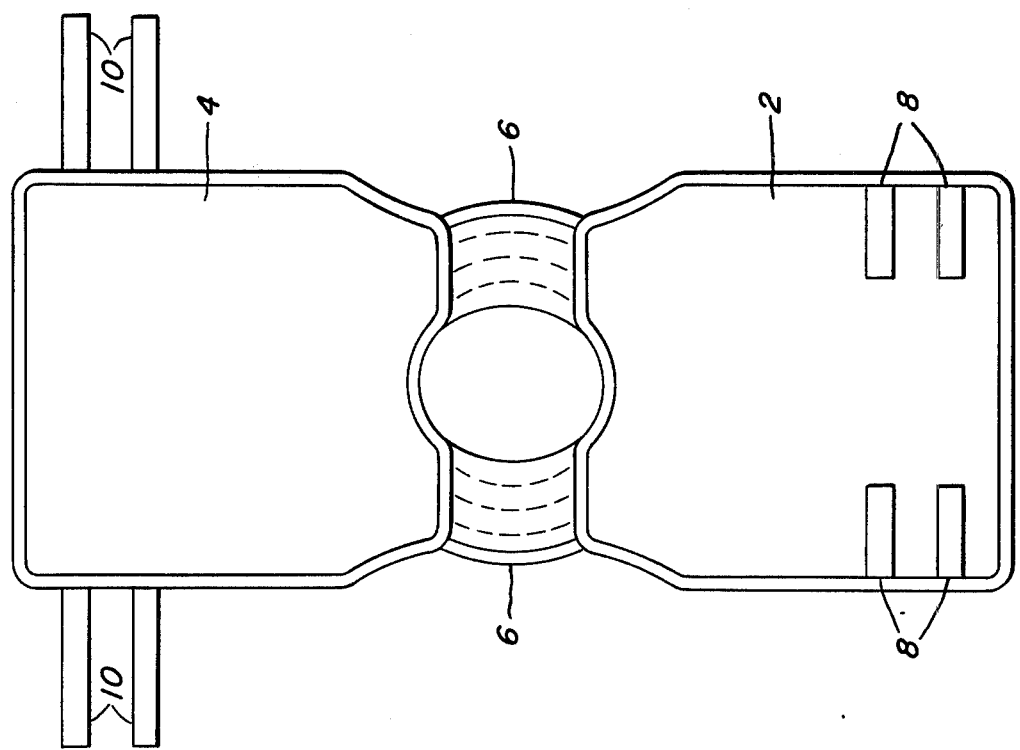
FIG. 2 is a plan view of the cooling garment of the present invention spread out in a flat position showing the outsides of the body panels.

The cooling garment of the present invention can best be understood from FIGS. 1 and 2. A front body panel 2 and a rear body panel 4 are connected at the tops by shoulder straps 6. The front and rear body panels are preferably formed from two layers of fabric such as an aluminized and rubberized Dacron with a foam layer disposed between the two layers of fabric, and the shoulder straps are preferably padded. The garment is designed in a pattern of a vest, open on the sides and secured by fasteners 8 and 10. First matable strip fasteners 8 and second matable strip fasteners 10 are preferably of the type known by the trademark Velcro, which can be secured in any position by pressure and may be removed merely by pulling the two pieces apart. Thus, when the garment is placed over the shoulders of the wearer with the head between the shoulder straps, the first matable strip fasteners 8 may be secured to the second matably strip fasteners 10, and the garment is secured to the body of the wearer.

Figure 3:
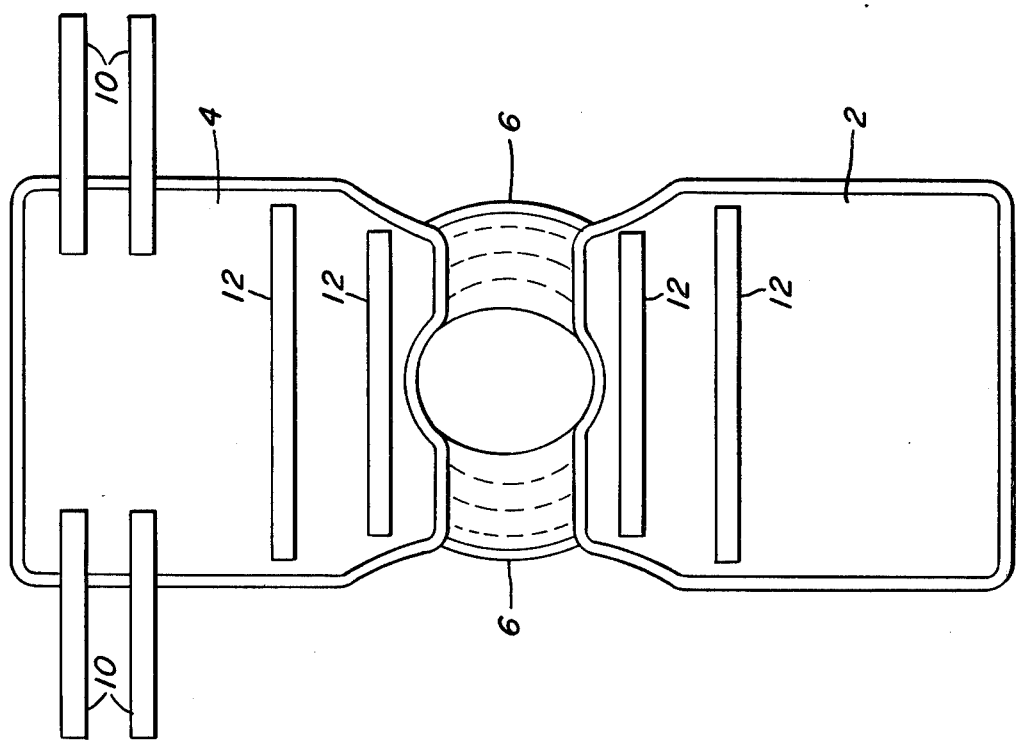
FIG. 3 is a view similar to FIG. 2 showing the inside of the body panels.
Figure 4:
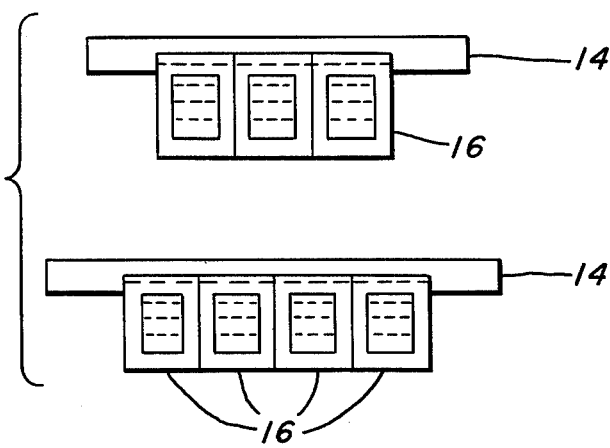
FIG. 4 is a detailed elevation view of the water-proof bags attached to the strip fastener of the present invention.
Figure 5:
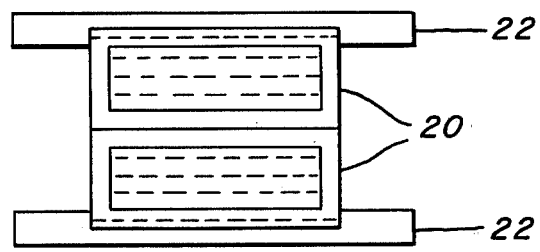
FIG. 5 is an elevation view of optional additional sealed water-proof bags for attachment to the present invention.

As shown in FIG. 3, third matable strip fasteners 12 are secured to the inside of the front and back body panels. The third matable strip fasteners 12 are releasably securable to fourth matable strip fasteners 14, which are shown in FIG. 4. Matable strip fasteners 12 and 14 are also preferably made from a material such as that known by the trademark Velcro. A plurality of pockets 16 are attached to the fourth matable strip fasteners 14. These pockets 16 are preferably formed from a heavy vinyl and each pocket 16 contains a sealed plastic bag containing water. The sealed plastic bags are made of a material which is resistant to boiling and freezing temperatures. In the preferred embodiment shown in the drawings where seven pockets 16 are attached to each of the front and rear body panels, the plastic bags preferably contain approximately 10 ounces of water each, so that the total weight of the water in the pockets 16 is 8¾ pounds. The garment itself weighs approximately one pound, so that the total weight of the garment in use is approximately ten pounds.

The pockets 16 are secured to the fourth matable strip fasteners 14 such that when the fourth matable strip fasteners 14 are secured to the third matable strip fasteners 12, the pockets 16 are secured within the inside of the garment. The number of pockets 16 used will depend upon the size and shape of the individual pockets 16 and of the garment, but a preferred arrangement is to have two fourth matable strip fasteners 14 attached to each of the front and rear body panels, with one of the fasteners 14 having three pockets 16 attached thereto and a second fastener 14 having four pockets 16 attached thereto, such that seven pockets 16 are attached to the front body panel and seven pockets 16 are attached to the rear body panel.

In use, the pockets 16 are placed in an ordinary freezer until the water in the bags is frozen. The pockets 16 are then removed from the freezer, and the fasteners 14 are secured to the fasteners 12 so that the frozen bags are secured to the inside of the garment. The garment is secured to the body of the wearer by attaching the fasteners 10 to the fasteners 12, and the garment cools the wearer until the ice in the bags has melted. This cooling period has been found to be approximately four hours at a temperature 40° C. at a work load of 1200 BTU's.

As shown in FIG. 1, a layer of absorbent material such as terry cloth 18 may be disposed between the pockets 16 and the body of the wearer. This serves as insulation between the wearer and the ice, and because of the temperature of the pockets, no further insulation is required between the pockets 16 and the individual except for a standard cotton undershirt. When the ice in the bags is completely melted and the cooling effectiveness of the garment has ended, the pockets 16 with the bags containing water may be removed by merely detaching fastener 14 from fastener 12, and new frozen pockets 16 may be attached to the garment. This allows the individual wearing the garment to proceed back into the hot location with minimal time required for changing the pockets 16.

There has been disclosed a cooling garment for use in heat stress environments, which garment is inexpensive, comfortable to wear, efficient, and functional. The present invention is advantageous over other garments of this type because the bags are inserted in pockets 16 and are thus doubly protected and sealed to reduce the possibility of leakage. The number of bags in the preferred embodiment is only 14, with the design of the bags being such that the garment does not become bulky. The insulation required to keep the cooling effectiveness of the garment close to the wearer's skin is provided by the structure of the front and back body panels, and no additional insulation or other garment is required. The design of the garment allows better cold air circulation throughout the jacket, because the pockets are located in a hanging fashion so that air can circulate on both sides of the ice pocket to be cooled. The pockets are attached in rows by means of strip fasteners which allow the pockets to be easily removed for freezing purposes and easily replaced if any of the pockets rupture. If one pocket does rupture, no significant inefficiency occurs since the remaining pockets continue to cool the wearer. The garment is comfortable to wear and does not hinder the wearer in his movements and breathing apparatus may be worn over the cooling garment. The padding in the shoulder straps 6 should be sufficient to accommodate such rescue breathing apparatus and allow for comfort during the wearing of such apparatus. The adjustable strip fasteners 10 and 12 allow the garment to be attached snugly to any individual regardless of size.

I claim:

1. A vest-like garment for cooling the body of the wearer, comprising:
   an insulated front panel;
   an insulated rear body panel;
   shoulder straps connecting the top of the front body panel to the top of the rear body panel;
   first matable strip fasteners secured to the sides of the front body panel;
   second matable strip fasteners, releasably attachable to the first matable strip fasteners, secured to the sides of the rear body panel, such that when the first matable strip fasteners are secured to the second matable strip fasteners, the garment is secured to the body of the wearer;
   third matable strip fasteners attached to the inside of the front and rear body panels;
   a plurality of sealed waterproof bags filled with water;
   fourth matable strip fasteners, releasably attachable to the third matable strip fasteners, each of said fourth matable strip fasteners being secured to a plurality of the sealed waterproof bags, such that, when the sealed waterproof bags are frozen and releasably secured to the inside of the garment by securing the fourth matable strip fasteners to the third matable strip fasteners, the garment cools the body of the wearer.

2. The cooling garment defined in claim 1 wherein the sealed waterproof bags are formed from a vinyl plastic.

3. The cooling garment of claim 1 wherein there are two third matable strip fasteners horizontally attached to each of the body panels of the garment, and four fourth matable strip fasteners, each attachable to one of the third matable strip fasteners, such that the sealed waterproof bags are disposed in two rows on each body panel.

4. The cooling garment defined in claim 1 including a layer of absorbent fabric disposed between the inside surface of the bags and the wearer of the garment.

5. The cooling garment defined in claim 4 wherein the absorbent fabric is terry cloth.

6. The cooling garment of claim 1 wherein the front and back body panels are each made from two layers of fabric having an insulating foam layer therebetween.

7. The cooling garment of claim 6 wherein the fabric is aluminized rubberized Dacron.

8. The cooling garment of claim 1 wherein the matable strip fasteners are of the type known by the trademark Velcro.

9. The cooling garment of claim 7 wherein the bags are enclosed in pockets, each of which pockets is attached to a fourth matable strip fastener.

10. The cooling garment of claim 9 wherein the pockets are formed from a vinyl plastic.

* * * * *